United States Patent [19]

Brox

[11] Patent Number: 4,780,316

[45] Date of Patent: Oct. 25, 1988

[54] GELATIN CAPSULE

[75] Inventor: Werner Brox, Beerfelden, Fed. Rep. of Germany

[73] Assignee: R.P. Scherer Corporation, Troy, Mich.

[21] Appl. No.: 914,122

[22] Filed: Oct. 1, 1986

Related U.S. Application Data

[63] Continuation of Ser. No. 670,739, Oct. 31, 1984, abandoned.

[30] Foreign Application Priority Data

Mar. 2, 1983 [GB] United Kingdom ................ 8305693
Feb. 27, 1984 [EP] European Pat. Off. ........ 84301238.6

[51] Int. Cl.$^4$ ........................ A61K 9/48; A61K 9/66
[52] U.S. Cl. .................................. 424/456; 424/451; 424/452; 424/455
[58] Field of Search ................ 424/451, 452, 455, 456

[56] References Cited

U.S. PATENT DOCUMENTS

| | | | |
|---|---|---|---|
| 2,172,357 | 9/1939 | Brown | 252/1 |
| 2,847,346 | 8/1959 | Vaughan | 424/37 |
| 2,870,060 | 1/1959 | Bryan | 424/37 |
| 2,870,062 | 1/1959 | Stanley | 424/37 |
| 2,889,252 | 6/1959 | Valentine | 424/37 |
| 3,520,971 | 7/1970 | Benford | 424/37 |
| 3,653,934 | 4/1972 | Rolle | 424/37 |
| 3,656,997 | 4/1972 | Cordes | 117/73 |
| 3,779,942 | 12/1973 | Bolles | 424/37 |
| 3,784,684 | 1/1974 | Bossert et al. | 424/37 |
| 4,002,718 | 1/1977 | Gardella et al. | 424/37 |
| 4,088,750 | 5/1978 | Cresswell et al. | 424/37 |
| 4,198,391 | 4/1980 | Grainger | 424/37 |
| 4,366,145 | 12/1982 | Stoopak et al. | 424/37 |
| 4,428,927 | 1/1984 | Ebert et al. | 424/37 |

FOREIGN PATENT DOCUMENTS 715879 6/1952 United Kingdom .
1135709 12/1968 United Kingdom .

OTHER PUBLICATIONS

Johnson et al., "The Comparability of Dosage Regimens of Lanoxin Tablets and Lanoxicaps," British Journal of Clinical Pharmacology 4, pp. 209-211 (1977).

Ebert, "Soft Elastic Gelatin Capsules: A Unique Dosage Form," reprints from *Pharmaceutical Technology* (Oct. 1977).

*Primary Examiner*—Shep K. Rose
*Attorney, Agent, or Firm*—Allegretti & Witcoff, Ltd.

[57] ABSTRACT

A pharmaceutical dosage unit form comprises one or more pharmaceutically active materials dissolved or suspended in a liquid polyethylene glycol and encapsulated in a soft gelatin capsule shell, in which the capsule shell comprises gelatin, a plasticizer therefor, and an embrittlement inhibiting composition comprising a mixture of sorbitol and at least one sorbitan. Preferably the polyethylene glycol also contains glycerin, sorbitol or propylene glycol.

5 Claims, No Drawings

GELATIN CAPSULE

This application is a continuation of application Ser. No. 670,739, filed Oct. 31, 1984, now abandoned.

BACKGROUND OF THE INVENTION

Field of the Invention and Description of the Prior Art

This invention is concerned with improvements in and relating to pharmaceutical compositions and, more particularly, is concerned with pharmaceutical compositions in dosage unit form encapsulated in soft gelatin capsules.

Pharmaceutical compositions in dosage unit form encapsulated in soft gelatin capsules (hereinafter simply referred to as "capsules") are well known and basically consist of a "fill", comprising one or more pharmaceutically active materials dissolved or dispersed in an appropriate liquid vehicle, encapsulated in a soft gelatin shell, generally comprising gelatin together with a plasticizer therefor such as glycerin.

On class of vehicle which has been proposed for use in the fill comprises the liquid polyethylene glycols, for example polyethylene glycols having a molecular weight from about 100 to 600. Certain pharmaceutically active ingredients, for example benzodiazepine type compounds such as temazepam and lormetazepam, have been shown to have improved bioavailability when administered as polyethylene glycol solutions in soft capsules.

However, the use of a liquid polyethylene glycol as a carrier vehicle has an attendant disadvantage in that the material is hygroscopic and tends to adsorb water from the shell and thereby embrittle it. This embrittlement may be enhanced by migration of the plasticizer from the shell into the fill. As a result of such embrittlement, which may take place over a matter of months or years, the shell loses its elasticity and, hence, its resistance to mechanical shocks which are, encountered in handling and transport of the capsules. In extreme cases the capsules may be sufficiently embrittled and/or suffer such mechanical shocks that a capsule is ruptured.

The problem is not so severe as to render capsules having a fill comprising a liquid polyethylene glycol vehicle useless. Many thousands, or indeed millions, of such capsules survive transport and handling without breakage. However, the problem does exist and is exacerbated by the fact that, since capsules are commonly packed together in several tens, hundreds or even thousands, one breaking, and therefore leaking, capsule can damage other capsules in the same package and thus render a large number of capsules useless.

SUMMARY OF THE INVENTION

It has now been found, in accordance with the present invention, that the problem of embrittlement may be reduced by incorporating in the shell sorbitol in admixture with one or more sorbitans and, possibly, other polyols, and at the same time incorporating glycerin, sorbitol or propylene glycol in the liquid polyethylene glycol vehicle of the fill of the capsules.

DETAILED DESCRIPTION OF THE PREFERRED EMBODIMENT

Accordingly, the invention provides a pharmaceutical dosage unit form comprising one or more pharmaceutically active materials dissolved or suspended in a liquid polyethylene glycol and encapsulated in a soft gelatin capsule shell, in which the capsule shell comprises gelatin, a plasticizer therefor and an embrittlement inhabiting composition comprising a mixture of sorbitol and one or more sorbitans.

Typically, the embrittlement inhibiting composition comprises from 25 to 45% by weight of sorbitol and from 20 to 30% by weight of sorbitans (the major proportion of the sorbitan component being 1,4-sorbitan) together with water (typically in an amount of 13 to 20% by weight) and other polyhydric alcohols, the mannitol content being from 0 to 6% by weight.

Preferably the polyethylene glycol also contains glycerin, sorbitol or propylene glycol. In this case, the amount of glycerin, sorbitol or propylene glycol dissolved in the liquid polyethylene-glycol fill is suitably from 1 to 20% by weight, preferably from 2 to 12% by weight, more preferably from 3 to 8% by weight.

The amount of sorbitol/sorbitan(s) mixture in the shell is suitably from 4 to 25% by weight, preferably from 6 to 20% by weight, more preferably from 9 to 15% by weight.

As noted above, the sorbitol/sorbitan(s) mixture may contain other polyhydric alcohols but in this case the total amount of sorbitol and sorbitan(s) in the whole sorbitol/sorbitan(s)/other polyhydric alcohol(s) mixture is suitably from 45 to 75% by weight, preferably from 55 to 66% by weight. The other polyhydric alcohols are suitably hydrogenated saccharides.

The total mixture suitably contains not more than 6% by weight of mannitol and preferably contains from 1 to 4% by weight, more preferably from 2 to 3% by weight of mannitol.

Suitable materials for introducing the sorbitol/sorbitan(s)/polyhydric alcohol(s) mixture into the capsule shell are concentrated aqueous solutions of polyhydric alcohols derived from the hydrolysis and partial hydrogenation of glucose syrup. An example of a suitable commercially available material is that sold under the Trade name "Anidrisorb 35/70". This product has the typical analysis listed below:

Components (% by weight of concentrated aqueous solutions):

| D Sorbitol | Sorbitans | Other polyols | Mannitol | Water |
|---|---|---|---|---|
| 25–46% | 20–30% | 20–25% | 0–6% | 13–20% |

In addition to the sorbitol/sorbitan(s) mixture, the gelatin material of the capsule shell will also contain a plasticizer, such as glycerin, propylene glycol or sorbitol (in addition the sorbitol in the sorbitol/sorbitane mixture), and this is suitably present in an amount of from 10 to 40% by weight, preferably from 25 to 45% by weight. Further the shell material may contain other conventional ingredients such as coloring agents (pigments or dyestuffs), and oxidant or preservative materials such as potassium sorbate and ethyl, methyl and propyl parabens.

The pharmaceutically active component of the compositions of the invention may be any of a wide variety of orally administrable pharmaceutical materials. Where the material is insufficiently soluble in the liquid polyethylene glycol vehicle, the fill may contain co-solvents, such as water or ethanol, or suspending or dispersing agents. Preferably, however, the pharmaceutical material is one soluble in the liquid polyethylene glycol vehicle such as the benzodiazepines type compounds mentioned above.

In order that the invention may be well understood the following examples are given by way of illustration only.

Soft gelatin capsules were produced having the fill composition and shell composition noted below.

EXAMPLE 1

Temazepam Capsules, 10 mg

| (a) Fill composition in mg per capsule | |
|---|---|
| Temazepam | 10 mg |
| Polyethylene glycol 400 | 230 mg |
| Glycerin | 13 mg |
| (b) Dry Shell Composition (% by weight) | |
| Gelatin | 52% |
| Glycerin | 32% |
| Anidrisorb 35/70 | 12% |
| Water | 5% |

EXAMPLE 2

Temazepam Capsules, 20 mg

| (a) Fill Composition in mg per capsule | |
|---|---|
| Temazepam | 20 mg |
| Polyethylene glycol | 460 mg |
| Glycerin | 26 mg |
| (b) Dry Shell Composition | |
| Gelatin | 51% |
| Glycerin | 32% |
| Anidrisorb 35/70 | 12% |
| Water | 5% |

EXAMPLE 3

Lormetazepam Capsules, 0.5 mg

| (a) Fill Composition in mg per capsule | |
|---|---|
| Lormetazepam | 0.5 mg |
| Polyethylene glycol | 115 mg |
| Glycerin | 6.5 mg |
| (b) Dry Shell Composition | |
| Gelatin | 51% |
| Glycerin | 32% |
| Anidrisorb 35/70 | 12% |
| Water | 5% |

EXAMPLE 4

Lormetazepam Capsules, 1 mg

| (a) Fill Composition in mg per capsule | |
|---|---|
| Lormetazepam | 1 mg |
| Polyethylene glycol | 230 mg |
| Glycerin | 13 mg |
| (b) Dry Shell Composition % by weight | |
| Gelatin | 51% |
| Glycerin | 32% |
| Anidrisorb 35/70 | 12% |
| Water | 5% |

EXAMPLES 5 AND 6

Soft elastic gelatin capsules were produced from a fluid gelatin composition comprising (in % by weight):

| Gelatin | 38.5% |
|---|---|
| Glycerol | 20.7% |
| Anidrisorb 35/70 | 8.8% |
| Water | 32.0% |
| filled with a liquid fill comprising (in % by weight): | |
| Temazepam | 3.92% |
| Polyethylene glycol 400 | 96.08% |

Two batches of capsules were produced, the first (Example 5) containing 10 mg of Temazepam per capsule and the second (Example 6) containing 20 mg of Temazepam per capsule.

By way of comparison, gelatin capsules were produced using the same fill but using a conventional shell forming composition comprising (in % by weight):

| Gelatin | 42.06% |
|---|---|
| Glycerol | 24.30% |
| Water | 33.64% |

Again two batches of capsules were produced, the first (Comparative Example 1) containing 10 mg of Temazepam per capsule and the second (Comparative Example 2) containing 20 mg of Temazepam percapsule.

The batches of capsules were stored at 20° C. for several months and the hardness of samples of the batches was tested at intervals using a Harais-Hardness tester. Basically, this instrument operates by compressing the capsule under test for 20 seconds between a plunger attached to a load cell and a platform which is automatically raised. Thus, in order to test a capsule, it is placed horizontally on the platform so that it is in contact with both the platform and the plunger. During the test, the platform rises automatically and the load cell indicator displays the value of the resistance of the capsule to the compressive force. After 20 seconds the test is completed and the value displayed represents the hardness of the capsule under test.

In practice it has been found, as a matter of experience, that a hardness of greater than 12 Newtons, measured as described above, indicates that breakage through embrittlement of the capsule may be expected as a particular problem.

The results of the tests are shown in Table 1.

TABLE 1

| | Hardness (Newtons) stored at 20° C. for | | | | |
|---|---|---|---|---|---|
| Example | 0 month | 1.7 months | 6.7 months | 7.8 months | 9.8 months |
| 6 | 8.0 | 9.6 | 11.5 | 12.16 | 12.3 |
| 6 | 5.25 | 8.0 | 10.4 | 11.2 | 11.9 |
| Comp. 1 | 9.95 | 11.65 | 13.75 | 13.65 | 13.75 |
| Comp. 2 | 7.3 | 10.6 | 12.75 | 13.25 | 13.2 |

It may be seen from these results that the capsules in accordance with the invention have generally lower initial hardnesses than comparable corrected capsules and that they have effective storage lives, considered as lives during which their hardness is 12 or less, at least twice as long as those of the comparable conventional capsules.

EXAMPLES 7 AND 8

Soft elastic gelatin capsules were produced from a fluid gelatin composition comprising (in % by weight):

| | |
|---|---|
| Gelatin | 40.67% |
| Glycerol | 18.02% |
| Anidrisorb 35/70 | 7.53% |
| Water | 33.58% |
| filled with a fill comprising (in % by weight): | |
| Temazepam | 3.92% |
| Glycerol | 5.0% |
| Water | 0.38% |
| Polyethylene glycol 400 | 90.2% |

Two batches of capsules were prepared, one (Example 7) containing 10 mg of Temezepam per capsule and the other (Example 8) containing 20 mg of temazepam per capsule.

The batches were divided into three lots and each lot was stored at a temperature of 20° C., 30° C., and 40° C., respectively. The hardness of the capsules were determined as described in Examples 5 and 6 to give the results shown in Table 2.

TABLE 2

| Example | Hardness (Newtons) stored for | | |
|---|---|---|---|
| (storage temperature - °C.) | 0 month | 1 month | 3.5 months |
| 7(20) | 7.93 | — | 10.60 |
| 7(30) | 7.93 | — | 11.32 |
| 7(40) | 7.92 | 11.34 | 10.43 |
| 8(20) | 6.91 | — | 10.22 |
| 8(30) | 6.91 | — | 11.23 |
| 8(40) | 6.91 | 10.20 | 11.05 |

I claim:

1. A pharmaceutical dosage unit form comprising a pharmaceutically active material, in a therapeutically effective amount, dissolved or suspended in a liquid polyethylene glycol having a mean molecular weight of from about 300 to 600 and encapsulated in a soft gelatin capsule shell, in which the capsule shell comprises gelatin, 10 to 40% by weight of a plasticizer therefor and 4 to 25% by weight of an embrittlement inhibiting composition consisting essentially of concentrated aqueous solutions of polyhydric alcohols derived from the hydrolysis and partial hydrogenation of glucose syrup, the concentrated aqueous solutions having the following typical analysis and components based on the percentage by weight of the concentrated aqueous solutions: D-sorbitol 25 to 45%, sorbitan 20 to 30%, other polyols which are suitably hydrogenated saccharides 20 to 25%, mannitol 1 to 6% and water 13 to 20%.

2. A dosage unit form as claimed in claim 1 in which the shell contains from 6 to 20% by weight of the embrittlement inhibiting composition.

3. A dosage unit form as claimed in claim 1 in which the polyethylene glycol also contains glycerin, sorbitol or propylene glycol.

4. A dosage unit form as claimed in claim 3 in which the glycerin, sorbitol or propylene glycol is present in the polyethylene glycol in an amount of from 1 to 20% by weight.

5. A dosage unit form as claimed in claim 1 in which the shell contains from 7 to 12% by weight of the embrittlement inhibiting composition.

* * * * *